United States Patent [19]

Coulston et al.

[11] Patent Number: 4,869,896
[45] Date of Patent: Sep. 26, 1989

[54] POTENTIATED INSECT REPELLENT COMPOSITION AND METHOD

[75] Inventors: Frederick Coulston, Alamogordo, N. Mex.; Friedrich W. A. G. K. Korte, Attenkirchen, Fed. Rep. of Germany

[73] Assignee: Angus Chemical Company, Northbrook, Ill.

[21] Appl. No.: 145,609

[22] Filed: Jan. 19, 1988

Related U.S. Application Data

[63] Continuation-in-part of Ser. No. 740,232, May 31, 1985, abandoned, which is a continuation of Ser. No. 615,521, May 30, 1984, abandoned.

[51] Int. Cl.[4] .................... A61L 9/04; A01N 43/16; A01N 37/18
[52] U.S. Cl. ............................ 424/45; 424/DIG. 10; 514/456; 514/617; 514/919
[58] Field of Search .................. 424/DIG. 10, 48; 514/456, 919, 617

[56] References Cited

U.S. PATENT DOCUMENTS

| | | | |
|---|---|---|---|
| Re. 29,829 | 11/1978 | Bordenca et al. | 549/302 |
| 1,995,247 | 3/1935 | Haring | 549/283 |
| 2,459,684 | 1/1949 | Croxall et al. | 549/300 |
| 2,731,475 | 1/1956 | Hillyer et al. | 549/302 |
| 2,991,220 | 7/1961 | Bruce | 514/86 |
| 3,089,877 | 5/1963 | Korte et al. | 549/283 |
| 3,923,997 | 12/1975 | Meuly | 549/300 |
| 4,064,268 | 12/1977 | Adolphi et al. | 514/86 |
| 4,414,227 | 11/1983 | Tomlinson, Sr. et al. | 514/690 |
| 4,416,881 | 11/1983 | McGovern et al. | 424/DIG. 10 |
| 4,419,360 | 12/1983 | Smolanoff | 514/210 |
| 4,424,215 | 1/1984 | Buerstinghaus et al. | 514/112 |
| 4,424,217 | 1/1984 | Reifschneider | 514/128 |
| 4,425,361 | 1/1984 | Lohmann et al. | 514/488 |
| 4,427,700 | 1/1984 | Retnakaran | 424/DIG. 10 |

FOREIGN PATENT DOCUMENTS

| | | |
|---|---|---|
| 1007555 | 5/1957 | Fed. Rep. of Germany . |
| 1007555 | 5/1957 | Fed. Rep. of Germany . |
| 1184774 | 1/1965 | Fed. Rep. of Germany . |
| 57-145867 | 10/1982 | Japan . |

OTHER PUBLICATIONS

R. Wegler, Chemie Der Pflanzenschutz-Und Schadlings-Bekampfungsmittel 488-489, (Springer-Verlag, Berlin 1970).
H. Schildknecht, Repellants Produced by Insects and Plants, Their Isolation and Characterization, 73 Agnew. Chem. 629 (1961).
H. Schildknecht, Defensive Substances of Arthropods, Their Isolation and Elucidation, 75 Angew. Chem. 762 (1963).
H. Schildknecht, Quinones as the Active Principle of the Defensive Substances of Diplopoda, 16b Z. Naturforschg. 810 (1961).
H. Schildknecht et al., The Defensive Substances of Some Carabidae, Especially Abax ater, 17b Z. Naturforschg.
M. Pavan, Extraction and Crystallization of Iridomyrmecin, 38 Chimica Industria. 625 (1955).
M. Pavan, Insects as a Source of Biologically Active Products, 37 Chimica Industria. 714 (1955).
T. Eisner et al., Cyanogenic Glandular Apparatus of a Millipede, 139 Science 1218 (1963).
T. Eisner, Catnip: Its Raison d'Etra, 146 Science 1318 (1964).
The Merck Index 669 (9th ed. 1976) ("Iridomyrmecin"; Abstract 4938).
The Merck Index 1015 (9th ed. 1976) ("Baygon"; Abstract (7625).
S. Bhargava et al., Studies in Cycloheptane Series: Part XVIII-Synthesis of Cis-Cycloheptan-1-ol-2-Carboxylic Acids, 9 INDIAN J. CHEM. 624-25 (1971).
1 H. Wegler, Chemie Der Pflanzenschutz- und Schadlings-Bekampfungsmittel 487-96, (Springer-Verglg, Berlin, 1970).
F. Korte et al., α-Hydroxyalkyliden-Lacton-Umlagerung-IX, 6 TETRADEDRON 201-16 (1959).
B. Belleau, The Prins Reaction with β,λ-Unsaturated Acids and Amides, 35 CANADIAN J. CHEM. 763-76 (1957).
48 Chem. Abstracts 896c (1954).
41 Chem. Abstracts 3575h (1946).

*Primary Examiner*—Allen J. Robinson
*Assistant Examiner*—Raymond J. Henley, III
*Attorney, Agent, or Firm*—Leydig, Voit & Mayer

[57] ABSTRACT

Potentiated insect repellent compositions comprising a combination of Deet and certain bicyclic lactones having insect repellent properties are disclosed. The lactones comprise compounds of the formula:

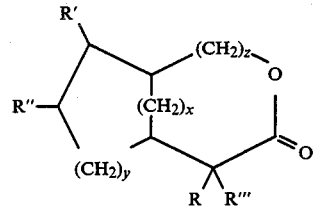

or the corresponding unsaturated compounds thereof having the formula:

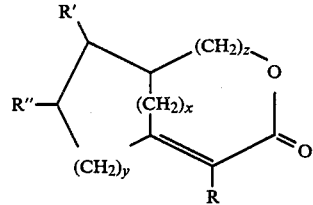

wherein R, R', R" and R'" each are lower alkyl or hydrogen; wherein y is an integer from 1-3, and x and z each are 0 or 1, with the proviso that y is 1 or 2 when x is 1. Preferably, R, R', R" and R'" each are hydrogen or methyl. Such compositions preferably further include a carrier. A method of using such a potentiated composition to repel an insect from a situs comprises applying to such situs an effective amount of the composition, with or without the carrier.

11 Claims, No Drawings

POTENTIATED INSECT REPELLENT COMPOSITION AND METHOD

This is a continuation-in-part application of our Ser. No. 740,232, filed May 31, 1985, now abandoned, as a continuation of our Ser. No. 615,521, filed May 30, 1984, now abandoned.

BACKGROUND OF THE INVENTION

The present invention is directed to potentiated insect repellent compositions comprising Deet (N,N-diethylmetatoluamide), and a class of bicyclic lactones having insect repellent activity.

The search for insect repellent compositions characterized by a combination of excellent repellent activity, high residual activity and relatively little or no toxicity to humans is a continuing one due to recognition of possible toxicity to humans or pets. Thus, relatively longlasting repellent compositions, having essentially no toxic effects upon humans, are currently in great demand.

Generally, commerically available insect repellent compositions comprise an insect repellent compound in a carrier. The cost of the repellent composition is based, to a large extent, upon the cost of the relative amount of repellent compound included therein. Accordingly, any reduction of the relative amount of repellent compound in the carrier while still achieving a strong insect repellent activity will result in a relatively less expensive and desirable commercial product.

Further, relatively high concentrations of Deet may give rise to allergic or toxic reactions in some individuals, as it is well known that different individuals may exhibit significantly different allergic reactions to a given substance. Also, at a certain concentration of Deet, a particularly sensitive individual may begin to exhibit signs of allergic reaction, whereas the same individual may not exhibit such a sensitivity when exposed to a second composition which includes a lesser amount of Deet.

Moreover, the odor or oily nature of Deet may become undesirable to some individuals at relatively high concentrations.

REPELLENTS: AS DISTINGUISHED FROM INSECTICIDES

Repellent substances are known to cause insects to be driven away from or to reject otherwise insect-acceptable food sources. Most known repellents, in fact, are not active poisons at all; but rather, prevent damage to plants or animals by making insect food sources or living conditions unattractive or offensive.

Repellents may be in the form of gases (olfactory), liquids, or solids (gustatory). Some well-known insect repellents include: benzil, benzyl benzoate; 2,3,4,5-bis(-butyl-2-ene) tetrahydrofurfural (MGK Repellent 11); butoxypolypropylene glycol; N-butylacetanilide; normal-butyl-6,6-dimethyl-5,6-dihydro-1,4,pyrone-2-carboxylate (Indalone); dibutyl adipate; dibutyl phthalate; di-normal-butyl succinate (Tabatrex); N,N-diethyl-meta-toluamide (also known as Delphone, Detamide, Autan, or, more simply, Deet); dimethyl carbate (cis-bicycol-[2.2.1]-5-heptene-2,3-dicarboxylate); dimethylphthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; and normal-propyl N,N-diethylsuccinmate. Standard repellents for mosquitoes, ticks, and the like are citronella oil, dimethyl phthalate, normal-butylmesityl oxide oxalate and 2-ethyl hexanediol-1,3. See Kirk-Othmer *Encyclopedia of Chemical Technology*, Second Edition, Volume 11, pps. 724–728; and *The Condensed Chemical Dictionary*, Eighth Edition, Page 756.

Cost considerations, moreover, often become important when choosing an effective repellent. A number of the above-mentioned repellents are only effective in relatively concentrated form. Commerically available repellent products, which may include Deet as the active repellent ingredient thereof, may include as much as 5–30% (or more) repellent in a carrier, based on total weight. U.S. Pat. No. 4,416,881 to McGovern et al., for example, discloses repellent concentrations of 6.25–25% repellent in a carrier. U.S. Pat. No. 4,419,360 to Smolanoff, in its test examples, discloses repellent concentrations of 5% repellent in a carrier.

Insecticides function by poisoning via oral ingestion of stomach (or other organ) poisons, by contact with the insect cuticle, or by fumigant action through the air. As is well known, the term "insect" refers to any member of a large group of invertebrate animals characterized, in the adult state (non-adult insect states include larva and pupa), by division of the body into head, thorax, and abdomen, three pairs of legs, and often but not always, two pairs of membranuous wings, viz., the dictionary definition of insects in addition to including beetles, bees, flies, wasps, mosquitoes, etc., also includes wood lice, mites, ticks, and the like.

As is well known, an insecticide is a type of pesticide designed to control insect life which is harmful to man. Such harm can be manifested either directly as disease vectors, or indirectly as destroyers of crops, food products, or textile fabrics. Several well-known insecticides include: inorganic compounds (such as arsenic, lead and copper); naturally occurring organic compounds (such as rotenone, pyrethrins, nicotine, copper naphthenate and petroleum derivatives); and synthetic organic compounds (such as DDT, dieldrin, endrin, chlordane, lindane, paradichlorobenzene and parathion).

Another group of organic insecticides acts on the principle of metabolic inhibition and, accordingly, are known as antimetabolites. Besides direct application onto a plant so as to be directly contactable by an insect (e.g., an insect larva), certain antimetabolites can be fed to growing plants either as a nutrient or a non-nutritional ingredient therefore with the result being that such a host plant will incorporate the antimetabolite into its plant tissue and, upon transfer of the antimetabolite into the insect via ingestion, no longer serve as a food source for the insect. See Kirk-Othmer *Encyclopedia of Chemical Technology*, 2nd Edition, published by John Wiley & Sons, Inc., Volume 11, pps. 667–738 (1966); and *The Condensed Chemical Dictionary*, 8th Edition, Published by Van Nostrand Reinhold Company, Pages 469–470 (1971).

It is thus generally well known that most insecticides are toxic to man in varying degrees.

PRIOR ART

In 1959, several investigators (viz., F. Korte, J. Falbe and A. Zschocke) of the Chemical Institute at Bonn University, West Germany, reported (in *Tetrahedron*, 1959, Volume 6, pp. 201–216) a number of generally applicable methods for synthesizing a variety of bicyclic gamma- and delta-lactones, including the method for synthesizing D,L-Iridomyrmecin. See also Korte et al. U.S. Pat. No. 3,089,977. In the Korte article, it was noted that some of the therein-disclosed compounds exhibited insecticidal properties. (One of the investigators, Korte, it will be noted, is a named coinventor herein.) It was only recently (1982), however, that the insecticidal properties of Iridomyrmecin and number of the other bicyclic lactones discussed in the *Tetrahedron* article were studied in somewhat greater detail by us. Significantly, no mention was ever made of the insect repellent activity of said lactones. That invention was more recently made and is reported herein.

Certain substances which enhance or otherwise augment the repellent activity of Deet are well known.

For example, in U.S. Pat. No. 4,427,700 to Retnakaran, it has been noted that a significant enhancement of repellent activity against the black fly (*Simulium venustum* Say, and *Prosiumulium hirtipes* Fries) has been obtained by the addition of vanillin (also known as 4-hydroxy-3-methoxybenzaldehyde), in relatively minor proportion, to Deet.

It is further known that certain Deet-based repellent compositions include additives which seem to enhance the repellent activity of Deet. During the course of our experimental work in connection with this invention, we have learned of five such known Deet-based repellent composition additives. See Table I. Some, but not all, of these additives are known to exhibit insect repellent activity.

TABLE I

| Additive Number | Additive Name |
|---|---|
| 1 | Allethrins[1] |
| 2 | Dimethyl Phthalate[2] |
| 3 | Di-normal-propyl isocinchomeronate[2] |
| 4 | Normal-octyl biycloheptene dicarboximide |
| 5 | 2,3:4,5-bis (2-butylene) tetrahydro-2-furaldehyde[3] |

[1]The allethrins (there are two: namely, Allethrin I and Allethrin II), also known as the allyl cinerins, are the synthetic analogs of the naturally-occurring insecticides cinerin, jasmolin, and pyrethiin. Allethrin I is 2,2-dimethyl-3-(2-methyl-1-propenyl)-cyclopropanecarboxylic acid 2-methyl-4-oxo-3-(2-propenyl)-2-cyclopenten-1-yl ester. Allethrin II is 3-(3-methoxy-2-methyl-3-oxo-1-propenyl)-2,2-dimethylcyclopropanecarboxylic acid 2-methyl-4-oxo-3-(2- propenyl)-2-cyclopenten-1-yl ester. (See The Merck Index, 9th Edition, published (1976) by Merck Co., Inc., page 36, No.242)
[2]Well-known repellents, briefly discussed above.
[3]A well-known repellent, briefly discussed above. (See MGK Repellent 11.)

From Table I it is readily apparent that the chemical structures provide no basis for predicting whether an additive will or will not enhance the repellent activity of Deet.

It will be noted also that none of the Deet-based repellent compositions additives indicated above in Table I is a lactone of the type we disclose herein.

It was pointed out in U.S. Pat. No. 4,427,700 that Deet, by itself, is primarily effective used only against mosquitoes, as it (Deet) is known to possess little or only mediocre repellent activity against a variety of other commonly-encountered bothersome insects, e.g., black flies (col. 1, 11. 36–38).

Bordenca et al., U.S. Pat. Reissue No. 29,829 discloses compositions containing secondary and tertiary hydroxylamines as insect repellents.

Croxall et al. U.S. Pat. No. 2,459,684 relates to lactones formed from half esters of substituted tetrahydrophthalic acid which are said to be useful as insecticidal toxicants and repellents. These compounds however differ greatly in structure from the present bicyclic lactones.

OBJECTS AND SUMMARY OF THE INVENTION

It is therefore a general object of this invention to provide novel potentiated insect repellent compositions which are effective repellents against a wide variety of insects, including ants, fleas, flies, mosquitoes, and the like.

A more specific object is to provide such compositions which include bicyclic lactones which themselves possess insect repellent activity.

A still more specific object is to provide certain bicyclic lactones which function in a cooperative manner with Deet such that the respective repellencies of the Deet or lactone or both are potentiated.

Yet another object is to provide insect repellent compositions which are substantially non-toxic or only mildly toxic to humans.

A further object is to provide methods of repelling insects using such potentiated compositions.

A potentiated insect repellent composition, as the term is used herein to define our invention, means a repellent composition which produces a result substantially in excess of that which reasonably could be expected or predicted from the known effect of the components either alone or addivively.

The combination of Deet with the Iridomyrmecin derivatives disclosed herein provides such a potentiated effect. While we do not wish to be committed to a specific theory of action, it appears that there is a cooperative effect over a rather wide ratio of either compound to the other, as more clearly seen hereinafter. Whatever the theory, the resulting composition is a strong, effective relatively less expensive and relatively less toxic repellent composition than either one taken alone. The result was unpredictable and surprising.

In accordance with the foregoing objects, the potentiated insect repellent composition of the present invention will now be summarized. The composition comprises Deet and a compound of the formula:

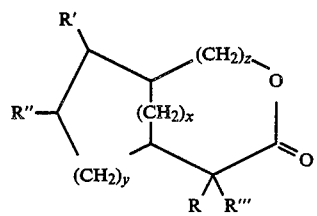

or the corresponding unsaturated compound thereof having the formula:

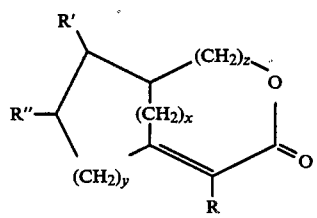

wherein R, R', R" and R''' each are lower alkyl (e.g., $C_1$–$C_4$) or hydrogen and R''' may be nonexistent; wherein y is an integer from 1–3, and x and z each are 0 or 1, with the proviso that y is 1 or 2 when x is 1. Preferably, R, R', R" and R''' each are hydrogen or methyl. Also preferably, the composition further comprises a carrier.

The foregoing, as well as other objects, features and advantages of the present invention will become more readily understood upon reading the following detailed description of the preferred embodiments.

DETAILED DESCRIPTION OF THE PREFERRED COMPOSITIONS

Considering the invention in one way, preferably, the repellent composition comprises Deet, a carrier, and about 0.025–10 weight percent of a bicyclic lactone of the class shown on Table II, based on the total weight of the composition. More preferably, the composition comprises 0.25–5 weight percent of a Table II bicyclic lactone, and up to 10 weight percent Deet, in a carrier.

Stating the invention alternatively within the foregoing context, our preferred compositions comprise a combination or mixture of a bicyclic lactone and the toluamide in an amount effective to repel insects, and a carrier, the mixture comprising the ratio of one part by weight of bicyclic lactone to each 0.025 to 10 parts by weight of the toluamide.

Of course it is possible to add either the lactone or Deet in amounts greater than indicated above. We have noted, however, that at higher concentrations there may be a masking effect of one component on the other so that the potentiation, through present, becomes difficult to observe in a biological test. In such higher concentrations the excess active ingredients may be wasted or unnecessary.

DETAILED DESCRIPTION OF THE PREFERRED LACTONES

Values of structural variables of the preferred bicyclic lactones, and abbreviations used below in Table II:

TABLE II

| Compound Abbreviation | is | x | y | z | R | R' | R'' | R''' |
|---|---|---|---|---|---|---|---|---|
| CIC-2 | sat. | 0 | 1 | 1 | $CH_3$ | $CH_3$ | H | H |
| CIC-3a | sat. | 0 | 2 | 1 | $CH_3$ | H | H | H |
| CIC-4 | sat. | 0 | 2 | 1 | H | H | H | H |
| CIC-5 | unsat. | 0 | 2 | 1 | $CH_3$ | H | H | non. |
| CIC-6 | sat. | 0 | 1 | 1 | H | H | H | H |
| CIC-7 | unsat. | 0 | 2 | 1 | H | H | H | non. |
| CIC-8 | sat. | 0 | 1 | 1 | $CH_3$ | H | H | H |
| CIC-9 | unsat. | 0 | 1 | 1 | H | H | H | non. |
| CIC-10 | unsat. | 0 | 1 | 1 | $CH_3$ | H | H | non. |
| CIC-20 | sat. | 0 | 2 | 0 | $CH_3$ | H | H | H |
| CIC-21 | sat. | 0 | 2 | 0 | $CH_3$ | H | $CH_3$ | H |
| CIC-22 | sat. | 0 | 2 | 0 | $CH_3$ | $CH_3$ | H | H |
| CIC-23 | sat. | 1 | 1 | 0 | $CH_3$ | H | H | H |
| CIC-24 | sat. | 1 | 1 | 0 | $CH_3$ | H | $CH_3$ | H |
| CIC-25 | sat. | 1 | 1 | 0 | $CH_3$ | $CH_3$ | H | H |
| CIC-26 | sat. | 0 | 3 | 1 | $CH_3$ | H | H | $CH_3$ | sat. = saturated
unsat. = unsaturated
non. = nonexistent

Somewhat more widely-recognizable names for these compounds are as follows. CIC-2 known as alpha-(2-hydroxymethyl-3-methyl-cyclopentyl) propionic acid lactone. Its trivial name is Iridomyrmecin. CIC-3a is known as alpha-(2-hydroxymethyl-cyclohexyl) propionic acid lactone. CIC-4 is known as (2-hydroxymethyl-cyclohexyl) acetic acid lactone. CIC-5 is known as alpha-(2-hydroxymethy-cyclohexylidene) propionic acid lactone. CIC-6 is known as (2-hydroxymethyl-cyclopentyl) acetic acid lactone. CIC-7 is known as (2-hydroxymethyl-cyclohexylidene) acetic acid lactone (see, B. Belleau, *Canadian Journal of Chemistry*, 35, 673 (1957)). CIC-8 is known as alpha-(2-hydroxmethyl-cyclopentyl) propionic acid lactone. CIC-9 is known as (2-hydroxymethyl-cyclopentylidene) acetic acid latone. CIC-10 is known as alpha-(2-hydroxymethyl-cyclopentylidene) propionic acid lactone. CIC-20 is known as alpha-(2-hydroxycyclohexyl) propionic acide lactone. CIC-21 is known as alpha-(2-hydroxy-4-methylcyclohexyl) propionic acid lactone. CIC-22 is known as alpha-(2-hydroxy-3-methylcyclohexyl) propionic acid lactone. CIC-23 is known as alpha-3-hydroxycyclohexyl) propionic acid lactone. CIC-24 is known as alpha-(3-hydroxy-4-methylcyclohexyl) propionic acid lactone. CIC-25 is known as alpha-(3-hydroxy-3-methylcyclohexyl) propionic acid lactone. CIC-25 is kown as alpha-(2-hydroxycycloheptyl) alpha, alpha-dimethyl propionic acid lactone.

The class of bicyclic lactones shown in Table II, including methods of synthesis thereof and tests demonstrating the insect repellent activities thereof, are discussed and disclosed in our copending patent application entitled INSECT REPELLENT, Ser. No. 615,522, filed May 30, 1984, now U.S. Pat. No. 4,663,346, which we now incorporate by reference. Bicyclic lactones (Table II) of such a class were recently discovered by us to have effective insect repellent activity. The Table II lactones, and the repellent compositions of the present invention, were moreover recently discovered by us to be effective non-contact repellents, viz., the insect is repelled, usually without having made contact with the repellent composition or host.

The nomenclature used in this patent has been used in the literature (including the *Tetrahedron* article briefly referred to above) and throughout the Chemical Abstracts up to 1966. After 1967, the Chemical Abstracts generally have used and now use the following names for the underlying CIC chemical skeletal structure, with the noted exception.

| CHEMICAL SKELETAL STRUCTURE | CHEMICAL ABSTRACTS NAME |
|---|---|
|  | 5,6,7,7a-Tetrahydrocyclopenta[c]pyran-3 (1H)—one |
|  | Hexahydrocyclopenta[c] pyran-3 (1H)—one |
|  | 1,5,6,7,8,8a-Hexahydro-3H—2-benzopyran-3-one |
|  | Hexahydro-3-isochromanone (up to 1972), (and after 1972) 1,1,4,5,6,7,8,8a-Octahydro-3H—2-benzo-pyran-3-one |
|  | Hexahydro-2(3H)—benzofuranone |

| CHEMICAL SKELETAL STRUCTURE | CHEMICAL ABSTRACTS NAME |
|---|---|
| | 2-Oxabicyclo [3.3.1] nonan-3-one |
| | Hexahydrocyclohepta [c] pyran-3(1H)—one |

METHODS OF USE

A method of using the repellent composition (of the present invention) to repel an insect from a situs comprises applying to such situs an effective amount of the repellent composition for thereby repelling the insect from the situs. Preferably, the repellent composition is used in combination with a carrier. Some carriers, it will be noted, can themselves have repellent properties.

The term "situs", as it is used throughout this application, will be understood to mean a position or location on specified plant or animal cells (or tissue) including a portion or location proximate or adjacent thereto.

The repellent compositions of the present invention thus can be formulated without a carrier or they can include suitable carriers for bringing the active (insect repellent) material into position for repelling common insect pests such as roaches, moths, house and stable flies, termites, flower beetles, bean beetles, weevils, ticks, chinch bugs, lice, ants, chiggers, mosquitoes, and the like.

Insects can be repelled by contacting the surfaces, on which such insects may alight or crawl, with a liquid, solid, or semi-solid composition. Such contact can be accomplished directly, e.g., by dispersing the composition into the air as by a liquid mist, in a manner such that the composition will fall on desired surfaces.

By way of further example, insect-infested animals, such as dogs with fleas, poultry with lice, cows with ticks, or monkeys (or other primates such as humans) with mosquitoes, can be treated with the insect repellent composition of the present invention, by contacting the skin, fur or features of such an animal with an effective amount of the composition for repelling the insect from the animal.

By way of yet further example, granaries and grain storage facilities such as silos can be treated with relatively minute effective amounts of the repellent composition (of the present invention), preferably prior to grain storage, to prevent beetle, weevil, and other insect infestations, otherwise present in the grain, thereby permitting such grain satisfactorily to be stored without fear of insect destruction.

In addition, food-packaging containers, including fiber, cardboard, and wooden shipping containers, storage bins, flour sacks, and the like, can be treated with relatively minute effective amounts of the composition with the present invention to prevent insect infestation.

The composition is usually applied directly by hand to the skin (of a person) or clothing area to be protected, but can also be mechanically sprayed on (as by an aerosol device). Alternatively, the active ingredients can be formulated into a paste of spreadable solid and applied from a tube or jar. Additional exemplary uses are discussed below.

CARRIERS

In the present invention, a variety of carriers (or diluents) for the above-disclosed insect repellent compositions can be used.

The carrier used can be any carrier conventionally used in insect repellent formulations. The carrier is preferably one that will not be harmful to the environment.

Accordingly, the carrier can be any one of a variety of commercially available organic and inorganic liquid, solid, or semi-solid carriers, or carrier formulations, including in aerosol form, usuable in formulating insect repellent products.

Examples of organic liquid carriers include liquid aliphatic hydrocarbons such as pentane, hexane, heptane, nonane, decane, and their analogs, as well as liquid aromatic hydrocarbons. Examples of other liquid hydrocarbons include oils produced by the distillation of coal and the distillation of various types and grades of petrochemical stocks, including kerosene oils which are obtained by fractional distillation of petroleum.

Other petroleum oils include those generally referred to (in the art) as agricultural spray oils, the so-called light and medium spray oils, consisting of middle fractions in the distillation of petroleum, and which are only slightly volatile. Such oils are usually highly refined and may contain only minute amounts of unsaturated compounds. Such oils are generally paraffin oils and accordingly can be emulsified with water and an emulsifier, diluted to lower concentrations, and used as sprays. Tall oils, usually obtained from sulfate digestion of wood pulp, can similarly be used.

Other organic liquid carriers can include liquid terpene hydrocarbons and terpene alcohols such as alphapinene, dipentene, terpineol, and the like.

In addition to the above-mentioned liquid hydrocarbons, the carrier can contain conventional emulsifying agents which can be used for causing the bicyclic lactone or Deet or both to be dispersed in, and diluted with, water for enduse applications.

Still other liquid carriers can include organic solvents such as aliphatic and aromatic alcohols, esters, aldehydes, and ketones. Suitable aliphatic monohydric alcohols include methyl, ethyl, normal-propyl, isopropyl, normal-butyl, sec-butyl, and tert-butyl alcohols. Suitable dihydric alcohols include glycols (such as ethylene and propylene glycol) and the pinacols (alcohols having the empirical formula $C_6H_{12}(OH)_2$). Situable polyhydroxy alcohols include gylcerol, arabitol, erythritol, sorbitol, and the like. Suitable cyclic alcohols include cyclopentyl and cyclohexyl alcohols.

Conventional aromatic and aliphatic esters, aldehydes, and ketones can be used as carriers, and occasionally are used in combination with the above-mentioned alcohols.

Still other liquid carriers which include relatively high-boiling petroleum products such as mineral oil, and higher alcohols (such as cetyl alcohol) can simularly be used.

Additionally, conventional or so-called "stabilizers", such as tert-butyl sulfinyl dimethyl dithiocarbonate, can be used in conjunction with, or as a component of, the carrier or carriers comprising the composition of the present invention.

Solid carriers which can be used in the composition of the present invention include finely divided organic and inorganic solid materials. Suitable finely divided solid inorganic carriers include siliceous minerals such as clay, bentonite, attapulgite, fuller's earth, diatomaceous earth, kaolin, mica, talc, finely divided quartz, and the like, as well as synthetically prepared siliceous materials, such as silica aerogels and precipitated and fume silicas.

Examples of finely divided solid organic materials include cellulose, sawdust, synthetic organic polymers, and the like.

Examples of semi-solid or colloidal carriers include waxy solids, gels (such as petroleum jelly), lanolin, and the like, and mixtures of well-known liquid and solid substances which can provide semi-solid carrier products, for providing effective repellency within the scope of the instant invention.

EXAMPLE 1 POTENTIATED REPELLENTS

Commerically-available Deet-based insect-repellent compositions generaly include a carrier. An exception is DEEP WOODS, a commercially available variety of Deet, which does not. Rather, it comprises 95 weight percent N,N-diethyl-meta-toluamide, the remaining 5 percent being the ortho-and para-toluamide isomers thereof. As was pointed out above in discussion directed to the '700 patent to Retnakaran, Deet, by itself, is a well-known mosquito repellent but is otherwise not very effective against a variety of other insects, such as black flies.

From one of our earlier tests (see data in Table III below) it is clear that the overall repellent effect of the insect repellent composition of the present invention is greater than the sum of the repellent activities of Deet and a bicyclic lactone (of the class shown in Table II), taken individually.

ual repellencies of the respective 0.25 weight percentages if CIC-2 and Deet in a carrier (as presented above in Table III), wherein the CIC-2 bicyclic lactone repellent and Deet compounds are shown, individually, to have repellent activities of less than one hour, it was unexpected and surprising to us to discover that a composition containing 0.25 weight percent of each of CIC-2 and Deet in a carrier yielded in insect repellent composition having an activity lasting four and one-half hours.

Similarly, 0.50 weight percent of Deet or of CIC-2 alone provided repellency for 3 hours but, in combination, they provide 7 hours. And, 0.25 weight percent of each in combination (total 0.50 weight percent) provided repellent activity 50 percent greater than obtained from 0.50 weight percent of either one alone.

TESTING PROCEDURES

The experimental procedures for Table III can be briefly summarized as follows: One milliliter of solution comprising each one of the Table III repellent compositions was initially applied to monkey stomach tissue with a cotton swab. (Each such surface to which a composition was applied was somewhat circular and about four inches in diameter.) Additional 0.2 milliliter quantities were used to saturate the swab. In some tests, the carrier solution was 50% aqueous acetone. In other tests, the carrier solution was aqueous 95% ethanol. During one repellency tests (in connection with the present invention), no noted differences as between the alcohol or acetone carriers were observed.

In our copending patent application, now U.S. Pat. No. 4,663,346, INSECT REPELLENT, incorporated by reference and mentioned above, it is reported that bicyclic lactones of the class shown in Table II are effective repellents against a wide variety of insects, including Solenopsis invicta (the imported Fire Ant);

TABLE III

| Repellent Compositions Comprising the Following Repellent Compound(s)[1] | %[2] | Total[3] % | mg per sq. cm.[4] | Time of Repellent Activity (hrs:mins.) | Remarks |
| --- | --- | --- | --- | --- | --- |
| CIC-2 | 0.25 | 0.25 | 0.066 | <1:00 | Little activity, many bit, test then terminated |
| Deet | 0.25 | 0.25 | 0.066 | <1:00 | Little activity, many bit, test then terminated |
| CIC-2 and | 0.25 | | | | terminated when |
| Deet | 0.25 | 0.50 | 0.132 | 4:30 | 6/30 bit |
| CIC-2 | 0.50 | 0.50 | 0.132 | 3:00 | terminated when 15/26 bit |
| Deet | 0.50 | 0.50 | 0.132 | 3:00 | terminated when 4/27 bit |
| CIC-2 and | 0.50 | | | | terminated when |
| Deet | 0.50 | 1.00 | 0.263 | 7:00 | 11/27 bit |
| CIC-3a and | 0.50 | | | | terminated when |
| Deet | 0.50 | 1.00 | 0.263 | 8:30 | a few bit. |

[1] As tested on Rhesus monkeys against Aedes aegypti (mosquitoes).
[2] Individual weight percentages of respective compounds in carrier.
[3] Total weight percent of repellent compounds in carrier.
[4] Approximate quantity of repellent compound(s), based on total weight percentage, per monkey-skin surface area.

It is apparent from Table III that a composition (or mixture) which includes at least one bicyclic lactone of the class shown in Table II in combination with Deet has been found to have insect repellent activity greater than the additive repellent effect that would be achieved from adding the respective repellencies of the lactone and Deet. For example, considering the individ- Aedes aegypti, Anopheles *quadrimaculatus, Anopheles albimanus, Culex salinarius* and *Culex nigripalpus* (different species of mosquitoes); *Stomoxys calcitrans* (stable fly); Drosophila (fruit fly); and *Xenopsylla cheopsis* (oriental rat flea).

EXAMPLE 2 COMBINATIONS OF CIC-4 LACTONE AND DEET

In a later but similar test procedure various combinations of CIC-4 lactone (2-hydroxymethylcyclohexyl acetic acid lactone) and Deet were applied in a carrier to Rhesus monkeys (*Macaca Mulatta*).

An application of 1.2 ml of test substance was made with an additional 0.2 ml added for cotton absorbency. The area of application on each animal was a circle of approximately 40 cm$^2$ in area. The tests substances were dissolved in Everclear ®grain alcohol, one hundred and ninety (190) proof.

Mosquitos used to test repellency were female *Aedes aegypti*, 5-7 days old. Prior to experimentation on the monkeys, the mosquitos were tested on humans as controls and they bit well. Cylindrical containers of clear plastic, with marquisette placed over both ends, were used to contain the mosquitos. The volume of the containers was about 375 cm$^3$. The open area of the marquisette-covered ends matches the area of application on the monkey.

Test substances were applied with a cotton swab. After one hour, testing began. Compounds were tested hourly for the first three hours, then usually on the half hour for longer periods of time. The results are summarized in Table IV.

TABLE IV

| Monkey Number | Compounds Tested | Ratio CIC/DEET | Repellency HRS. | Total Concentration |
|---|---|---|---|---|
| 1 | CIC-4 | | 3.0 | 2% |
| 2 | DEET | | 3.5 | 2% |
| 3 | CIC-4 (.18%) DEET (1.82%) | 1:10 | 5.5[1] | 2% |
| 4 | CIC-4 (.4%) DEET (1.6%) | 1:4 | 5.5[1] | 2% |
| 5 | CIC-4 (.66%) DEET (1.33%) | 1:2 | 5.0 | 2% |
| 6 | CIC-4 (1%) DEET (1%) | 1:1 | 5.5[1] | 2% |
| 11 | CIC-4 (2%) DEET (2%) | 1:1 | 9.0 | 4% |

[1] Repellency activity extended to >5½ hours without breakthrough.
Breakthrough is the point at which 2-5 or more mosquitos landed and started biting, with blood in insect.

EXAMPLE 3 REPELLENT ACTIVITY OF CIC-4 AND DEET COMBINATION

In another earlier but similar test the active ingredients, CIC-4, DEET, and combinations thereof, were dissolved in ethanol and applied in varying concentrations to the shaved bellies of Rhesus monkeys. 1 ml of the ethanol solution was applied to a circle of approximately 40 cm$^2$.

Mosquitoes (female *Aedas aegypti*) were brought into contact with the treated and control areas through a cylindrical vial of the same description as set forth above in Example 1.

Twenty to thirty mosquitoes were placed in the vial to evaluate repellency. Prior to bringing them into contact with the treated areas, the mosquitoes were brought into contact with a shaved, untreated area of the monkey's thigh to ensure the mosquitoes were biting.

A "fresh" vial, i.e., one which previously had not been exposed to treated areas, was brought into contact with the treated area for two minute durations at thirty minute intervals. Breakthrough in this Example is defined as the time at which a single bit is observed or multiple landings appeared to negate a repellent effect.

The results of this experiment are set forth in Table V below.

TABLE V

| Run # | Total (wt %) | CIC-4 (wt %) | DEET (wt %) | Breakthrough (hrs) |
|---|---|---|---|---|
| 1 | 0.25 | — | 0.25 | 1.0 |
| 2 | 0.25 | 0.25 | — | 1.5 |
| 3 | 0.50 | 0.25 | 0.25 | 3.0 |
| 4 | 0.50 | — | 0.50 | 2.0 |
| 5 | 0.50 | 0.5 | — | 2.5 |
| 6 | 1.0 | — | 1.0 | 3.0 |
| 7 | 1.0 | 1.0 | — | 3.5 |
| 8 | 1.0 | 0.75 | 0.25 | 4.5 |
| 9 | 2.0 | 2.0 | — | 4.5 |
| 10 | 2.0 | 1.75 | 0.25 | 6.5 |
| 11 | 4.0 | 4.0 | — | 7.0 |
| 12 | 4.0 | 3.75 | 0.25 | 10.0 |

EXAMPLE 4 REPELLENT ACTIVITY OF CIC-7 AND DEET COMBINATIONS

The active ingredients, CIC-7 (2-hydroxymethylcyclohexylidene acetic acid lactone), DEET, and combinations thereof, were applied in varying concentrations to the shaved bellies of Rhesus monkeys in 1.2 ml of an ethanol solution. The area of application was a circle of approximately 40 cm$^2$.

Mosquitoes (female *Aedas aegypti*) were brought into contact with the treated and control areas through a cylindrical vial of the same description as set forth above in Example 2.

Ten to fifteen mosquitoes were placed in the vial to evaluate repellency. Prior to bringing them into contact with the treated area, the mosquitoes were brought into contact with an untreated area of a control monkey to ensure that the mosquitoes were biting.

A fresh vial was brought into contact with the treated area for two minute durations at 30 minute intervals for the first three hours, hourly for the next three hours, and every half hour until breakthrough occurred. Breakthrough in this Exmaple is defined as the time at which a single bite with multiple landings occur.

The results of this experiment are set forth in Table VI below.

TABLE VI

| Run # | Total (wt %) | CIC-7 (wt %) | DEET (wt %) | Breakthrough (hrs) |
|---|---|---|---|---|
| 1 | 0.5 | — | 0.5 | 0.33* |
| 2 | 0.5 | 0.5 | — | 0.33* |
| 3 | 0.5 | 0.25 | 0.25 | 2.5 |
| 4 | 1.0 | 1.0 | — | 2.5 |
| 5 | 1.0 | 0.75 | 0.25 | 3.0 |
| 6 | 2.0 | 2.0 | — | 4.0 |
| 7 | 2.0 | 1.75 | 0.25 | 5.0 |
| 8 | 4.0 | 4.0 | — | 6.5 |
| 9 | 4.0 | 3.75 | 0.25 | 7.5 |
| 10 | 2.0 | 2.0 | | 4.5 |
| 11 | 2.0 | 0.66 | 1.33 | 7.0 |

*little or no repellent activity

EXAMPLE 5 REPELLENT ACTIVITY OF CIC-3a AND DEET COMBINATIONS

The active ingredients, CIC-3a (2-hydroxymethylcyclohexyl propionic acid lactone), DEET, and combinations thereof in varying concentrations were applied to the shaved bellies of Rhesus monkeys. 1.2 milliliter (ml)

of an ethanol solution of the compositions was applied to a circle of approximately 40 cm².

Mosquitoes (female *Aedas aegypti*) were brought into contact with the treated and control areas through a cylindrical vial (approximately 375 cm³) where both otherwise open ends were covered with a marquisette cloth through which the mosquitoes were able to bite. The cloth also ensured adequate ventilation through the vial. The open ends were approximately 38 cm² in area.

Ten to fifteen mosquitoes were placed in the vial to evaluate repellency. Prior to bringing them into contact with the treated monkey, the mosquitoes were brought into contact with an untreated area of a control monkey to ensure that the mosquitoes were biting.

The results of this experiment are set forth in Table VII below, wherein the total concentration of the active ingredients, concentration of CIC-3a and DEET, and the duration of observed repellency are recorded.

TABLE VII

| Run # | Total (wt %) | CIC-3a (wt %) | DEET (wt %) | Breakthrough (hrs) |
|---|---|---|---|---|
| 1 | 0.125 | — | 0.125 | 0.5* |
| 2 | 0.06 | 0.06 | — | 1.0 |
| 3 | 0.25 | 0.25 | — | 1.0 |
| 4 | 1.0 | 1.0 | — | 2.5 |
| 5 | 4.0 | 4.0 | — | 8.0 |
| 6 | 0.185 | 0.06 | 0.125 | 1.5 |
| 7 | 0.375 | 0.25 | 0.125 | 1.5 |
| 8 | 1.125 | 1.0 | 0.125 | 4.0 |
| 9 | 4.125 | 4.0 | 0.125 | 8.0 |
| 10 | 2.0 | 2.0 | — | 4.0 |
| 11 | 2.0 | 0.66 | 1.33 | 7.5+ |

*Little or no repellent activity.

EXAMPLE 6

A potentiated repellent composition is compounded in the following formula:

| | Wt. % |
|---|---|
| Deet | 20.0 |
| 2,3:4,5-bis(butylene) tetrahydro furaldehyde | 1.0 |
| N—octyl bicycloheptene dicarboximide | 4.0 |
| CIC-4 | 2.0 |
| aqueous alcohol | qs. |

This is a commercial type Deet formula with 2% CIC-4 added to increase the duration of effective repellency over a simliar formula alone which contains no CIC-4.

EXAMPLE 7

A potentiated repellent composition is compounded in the following formula:

| | Wt. % |
|---|---|
| Deet | 10.0 |
| CIC-4 | 2.0–4.0 |
| aqueous alcohol | qs. |

This is a commerical type formula employing CIC-4 to enhance duration of repellancy while reducing the amount of Deet, thereby lowering the toxicity of the composition. Optionally, other known repellents of the types listed above at pages 3 and 7 may be added if desired.

In evaluating the foregoing examples it should be borne in mind that a biological test of this kind necessarily involves the ues of numerous different animals and different batches of insets, as well as such variables as weather conditions. Therefore the data is not as numerically precise as an in vitro test, and some variations in the actual numerical readings from one series of tests to the other are inevitable but are within the skill of an experienced toxicologist to evaluate and draw valid conclusions. Such a person will focus on the overall effect observed in all of the tests under all circumstances rather than attaching undue significance to an individual test result taken out of context.

We believe the foregoing data to show the decided and unexpected benefits of a composition or mixture of Deet and the subject bicyclic lactones as practical insect repellents of relatively low toxicity.

Described herein are potentiated insect repellent compositions and methods of use thereof. While the repellent compositions of the instant invention have been presented and described with reference to preferred embodiments, the invention is not limited thereto. Alternatives, changes or modifications may become apparent to those skilled in the art upon reading the foregoing description, and such alternatives, changes and modifications are to be considered as forming a part of the invention insofar as they fall within the spirit and scope of the appended claims.

We claim:

1. A potentiated insect repellent composition comprising as active repellent ingredients a potentiatingly effective amount of the mixture of (a) N,N-diethylmetatoluamide and (b) a bicyclic lactone compound of the formula:

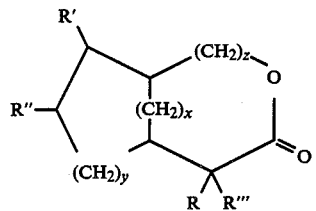

or the corresponding unsaturated compound thereof having the formula:

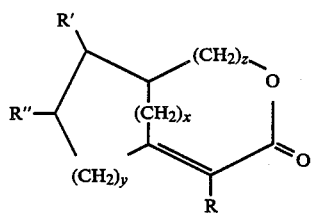

wherein R, R' and R'' each are methyl or hydrogen and R''' is either methyl or hydrogen or is nonexistent; wherein y is an integer from 1–3, and x and z each are 0 or 1, with the proviso that y is 1 or 2 when x is 1, in an amount effective to repel insects and optionally a carrier, said composition comprising a ratio of one part of weight of said bicyclic lactone to each 0.03125 to 10 parts by weight of said toluamide.

2. The composition of claim 1 wherein R, R', R'' and R''' each are hydrogen or methyl.

3. The composition of claim 1 wherein said composition comprises about 0.25–10 weight percent of said bicyclic lactone and about 0.25–20 weight percent of said toluamide.

4. The composition of claim 1, wherein said composition comprises said active ingredients in a ratio of one part of weight of said bicyclic lactone to each 0.5 to 10 parts by weight of said toluamide.

5. The composition of claim 1 wherein said carrier comprises an aerosol composition adapted to disperse said active ingredients into the atmosphere by means of a compressed gas.

6. The composition of claim 1 wherein said carrier is an aqueous ethanol or acetone solution.

7. The method of repelling insects from a situs comprising applying to said situs a potentiatingly effective amount of the composition of claim 1 to repel said insects.

8. The method of claim 7 wherein said composition further includes a carrier.

9. The method of claim 8 wherein said composition comprises about 0.25–10 weight percent of said bicyclic lactone and about 0.25–20 weight percent of said toluamide in said carrier.

10. The method of claim 7 wherein said composition comprises said active ingredients in a ratio of one part by weight of said bicyclic lactone to each 0.5 to 10 parts by weight of said toluamide.

11. The method of claim 7 wherein said carrier comprises an aerosol composition adapted to disperse said active ingredients into the atmosphere by means of a compressed gas.

* * * * *

UNITED STATES PATENT AND TRADEMARK OFFICE
CERTIFICATE OF CORRECTION

PATENT NO. : 4,869,896
DATED : Sep. 26, 1989
INVENTOR(S) : Frederick Coulston, Friedrich W. A. G. K. Korte It is certified that error appears in the above—identified patent and that said Letters Patent is hereby corrected as shown below:

Col. 1, line 50, insert after repellents, -- are only mildly toxic. A few of the known repellents, --.

Col. 5, line 36, insert after abbreviations used -- throught this application to refer to such lactones, appear --.

Col. 6, lines 15 & 16, delete "CIC-25 is kown" and replace with -- CIC-26 is known --.

Signed and Sealed this

Third Day of December, 1991

Attest:

HARRY F. MANBECK, JR.

*Attesting Officer*    *Commissioner of Patents and Trademarks*